United States Patent
Tsushima et al.

(10) Patent No.: US 11,260,003 B2
(45) Date of Patent: Mar. 1, 2022

(54) ANTIMICROBIAL COMPOSITION AND COSMETIC CONTAINING ANTIMICROBIAL COMPOSITION

(71) Applicant: ADEKA CORPORATION, Tokyo (JP)

(72) Inventors: Yasuhiro Tsushima, Tokyo (JP); Hiroshi Suzuki, Tokyo (JP); Makiko Yazawa, Tokyo (JP); Shotan Yamashita, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 88 days.

(21) Appl. No.: 16/754,002

(22) PCT Filed: Oct. 3, 2018

(86) PCT No.: PCT/JP2018/037009
§ 371 (c)(1),
(2) Date: Apr. 6, 2020

(87) PCT Pub. No.: WO2019/073874
PCT Pub. Date: Apr. 18, 2019

(65) Prior Publication Data
US 2020/0345602 A1    Nov. 5, 2020

(30) Foreign Application Priority Data
Oct. 11, 2017   (JP) ............................ JP2017-197709

(51) Int. Cl.
*A61K 8/34* (2006.01)
*A01N 31/02* (2006.01)
(52) U.S. Cl.
CPC ................ *A61K 8/34* (2013.01); *A01N 31/02* (2013.01)
(58) Field of Classification Search
CPC . A61K 8/33; A61K 8/34; A61K 8/345; A61K 8/365; A61K 8/44; A61K 8/498; A61K 8/55; A61K 8/60; A61Q 17/005; A61Q 19/00
See application file for complete search history.

(56) References Cited

U.S. PATENT DOCUMENTS 10,137,069 B2 * 11/2018 Tsushima ............... A61Q 19/00

FOREIGN PATENT DOCUMENTS

| EP | 2 807 925 | 12/2014 |
|---|---|---|
| JP | 11-322591 | 11/1999 |
| JP | 2002-322090 | 11/2002 |
| JP | 2003-81736 | 3/2003 |
| JP | 2004-43336 | 2/2004 |
| JP | 2007-16018 | 1/2007 |
| JP | 2007-84464 | 4/2007 |
| JP | 2011-57647 | 3/2011 |
| JP | 2013-216629 | 10/2013 |
| JP | 2014-5209 | 1/2014 |
| WO | 2006/136330 | 12/2006 |
| WO | 2015/125392 | 8/2015 |
| WO | 2017/121538 | 7/2017 |

OTHER PUBLICATIONS

International Search Report dated Dec. 18, 2018 in International Application No. PCT/JP2018/037009.
Extended European Search Report dated Jun. 22, 2021 in European Patent Application No. 18865529.4.
"Lightening Serum", MINTEL, Aug. 22, 2017, pp. 1-2.
"Cream Foil Mask", MINTEL, May 16, 2017, pp. 1-4.
"Dazzling Halo Radiant Fluid", MINTEL, Apr. 27, 2016, pp. 1-6.

* cited by examiner

*Primary Examiner* — Nannette Holloman
(74) *Attorney, Agent, or Firm* — Wenderoth, Lind & Ponack, L.L.P.

(57) ABSTRACT

An antimicrobial composition containing: a component (A) that is at least one selected from the group consisting of 1,2-alkanediols having an alkyl group having 6 to 8 carbons and monoalkyl glyceryl ethers having an alkyl group having 6 to 8 carbons; and a component (B) that is at least one selected from the group consisting of tripropylene glycol, 2-methyl-1,3-propanediol, and 3-methyl-1,3-butanediol and a cosmetic containing the antimicrobial composition.

7 Claims, No Drawings

ANTIMICROBIAL COMPOSITION AND COSMETIC CONTAINING ANTIMICROBIAL COMPOSITION

TECHNICAL FIELD

The present invention relates to an antimicrobial composition that exhibits significantly high antimicrobial activity and is less of an irritant to the skin while having a high level of safety for the human body, and also relates to a cosmetic.

BACKGROUND ART

An antimicrobial agent and/or an antifungal agent is commonly used in cosmetics with the goal of, e.g., preservation. Parabens have been used for these antimicrobial/antifungal agents, but the number of individuals experiencing allergic reactions to parabens has been increasing in recent years. As a result, there has been demand for antimicrobial compositions that exhibit a high level of safety for the human body while supporting a reduction in the amount of paraben or paraben replacement.

In this regard, the use of diol compounds, e.g., alkanediols, alkyl glyceryl ethers, and so forth, and their mixtures as antimicrobial agents is known. Patent Document 1 discloses an antimicrobial agent comprising a diol compound having a residue provided by the removal of one hydroxyl group from an at least trihydric alcohol. Patent Document 2 discloses a cosmetic composition that contains 2-ethylhexyl glyceryl ether. Patent Document 3 discloses an antimicrobial agent that is characterized by an α-monoalkyl glyceryl ether. Patent Document 4 discloses a cosmetic that contains water, an oil-soluble component, and hexyl glyceryl ether. Patent Document 5 discloses a preservative antimicrobial agent that combines a 1,2-alkanediol with at least one selection from Kankohso 201 (pionin), benzoic acid and its salts, phenoxyethanol, and 4-isopropyl-3-methylphenol. Patent Document 6 discloses an antimicrobial composition that contains a cationized β-glucan and an alkanediol compound and/or a glyceryl ether compound. These compositions exhibit good performance as antimicrobial agents, while exhibiting a high level of safety for the human body because they do not use parabens.

CITATION LIST

Patent Documents

[Patent Document 1] Japanese Patent Application Laid-open No. 2007-016018
[Patent Document 2] Japanese Patent Application Laid-open No. 2007-084464
[Patent Document 3] Japanese Patent Application Laid-open No. 2004-043336
[Patent Document 4] Japanese Patent Application Laid-open No. 2011-057647
[Patent Document 5] Japanese Patent Application Laid-open No. H11-322591
[Patent Document 6] Japanese Patent Application Laid-open No. 2014-005209

SUMMARY OF INVENTION

Technical Problem

These antimicrobial agents exhibit high safety for the human body, but in some instances they exhibit insufficient antimicrobial activity or antifungal activity for use as an antimicrobial/antifungal agent and must be added in large amounts to cosmetics. An improved antimicrobial performance has thus been desired for these antimicrobial agents.

Accordingly, an object of the present invention is to provide an antimicrobial composition that exhibits significantly high antimicrobial activity while having a high level of safety for the human body.

Solution to Problem

Upon carrying out intensive investigations, the present inventors then discovered that an antimicrobial composition having significantly high antimicrobial activity is provided by the combination of specific compounds having high skin safety, and achieved the present invention as a result.

That is, the present invention relates to an antimicrobial composition, containing:

a component (A) that is at least one selected from the group consisting of 1,2-alkanediols having an alkyl group having 6 to 8 carbons and monoalkyl glyceryl ethers having an alkyl group having 6 to 8 carbons; and a component (B) that is at least one selected from the group consisting of tripropylene glycol, 2-methyl-1,3-propanediol, and 3-methyl-1,3-butanediol.

Advantageous Effects of Invention

The present invention can thus provide an antimicrobial composition and a cosmetic that exhibit a significantly high antimicrobial activity while exhibiting little skin irritancy and an excellent moisturizing performance while having a high level of safety for the human body. In addition, the antimicrobial composition according to the present invention can be used as an antimicrobial agent that either supports a reduction in the amount of the parabens heretofore frequently used in cosmetics, or that can replace all or a portion of the parabens.

DESCRIPTION OF EMBODIMENTS

The component (A) used by the present invention is a 1,2-alkanediol having an alkyl group having 6 to 8 carbons or a monoalkyl glyceryl ether having an alkyl group having 6 to 8 carbons. Component (A) may contain both a 1,2-alkanediol having an alkyl group having 6 to 8 carbons and a monoalkyl glyceryl ether having an alkyl group having 6 to 8 carbons.

1,2-Alkanediols having an alkyl group having 6 to 8 carbons can be exemplified by 1,2-alkanediols having a straight-chain alkyl group having 6 to 8 carbons and 1,2-alkanediols having a branched alkyl group having 6 to 8 carbons, for example, 1,2-hexanediol, 1,2-heptanediol, and 1,2-octanediol, and a single one of these may be used or two or more may be used. Among the preceding, 1,2-octanediol is preferred from the standpoint of the synergetic effect on the antimicrobial activity through the combination with component (B) and a high antimicrobial activity.

The monoalkyl glyceryl ether having an alkyl group having 6 to 8 carbons is a monoalkyl glyceryl ether having a straight-chain alkyl group having 6 to 8 carbons, a branched alkyl group having 6 to 8 carbons, or a cycloalkyl group having 6 to 8 carbons. This straight-chain alkyl group, branched alkyl group, and cycloalkyl group can be exemplified by a hexyl group, a secondary-hexyl group, a heptyl group, a secondary-heptyl group, an octyl group, a 2-ethylhexyl group, a secondary-octyl group, a cyclohexyl group, a methylcyclohexyl group, a dimethylcyclohexyl group, a cycloheptyl group, and a methylcycloheptyl group. When the number of carbons in the alkyl group in the monoalkyl glyceryl ether is less than 6, the antimicrobial activity is then low and use as an antimicrobial agent is not possible. When, on the other hand, the number of carbons in the alkyl group in the monoalkyl glyceryl ether is greater than 8, a strong skin irritancy may be evidenced in addition to a decline in the antimicrobial activity. The water solubility also deteriorates, which impedes incorporation in aqueous solution products. A single one of these monoalkyl glyceryl ethers having a straight-chain alkyl group, branched alkyl group, or cycloalkyl group may be used or two or more may be used. Among the preceding, monoalkyl glyceryl ethers having a straight-chain alkyl group having 6 to 8 carbons or a branched alkyl group having 6 to 8 carbons are preferred from the standpoint of the synergetic effect on the antimicrobial activity through the combination with component (B) and a high antimicrobial activity, while 2-ethylhexyl glyceryl ether or octyl glyceryl ether is preferred. Through the use of such monoalkyl glyceryl ethers, an antimicrobial composition exhibiting both greater safety and antimicrobial activity can be obtained when these are used in combination with component (B).

The component (B) used in the present invention is tripropylene glycol, 2-methyl-1,3-propanediol, or 3-methyl-1,3-butanediol, and a single one of these or two or more may be used. By using such a component as the component (B), the antimicrobial effect of the component (A) in the cosmetic can be enhanced and an antimicrobial composition having a high antimicrobial activity can be obtained; in addition, an antimicrobial composition that exhibits little skin irritancy and an excellent moisturizing capability can be obtained. Among the preceding, tripropylene glycol or 2-methyl-1,3-propanediol is preferred from the standpoint of the enhancement in the antimicrobial effect of component (A), while 2-methyl-1,3-propanediol is particularly preferred.

The antimicrobial composition according to the present invention contains the component (A) and the component (B) that have been described in the preceding, and exhibits significant synergetic effects due to the incorporation of these components and can express a high antimicrobial activity.

There are no particular limitations on the content of the component (A) and the component (B) in the antimicrobial composition according to the present invention; however, from the standpoint of the antimicrobial activity the mass ratio between the component (A) and the component (B) is preferably 1:2 to 1:500, more preferably 1:5 to 1:400, still more preferably 1:10 to 1:300, even more preferably 1:13 to 1:300, and most preferably 1:15 to 1:200. Among these mass ratios, when, for example, the component (A) is at least one selected from the group consisting of 1,2-alkanediols having an alkyl group having 6 to 8 carbons, monoalkyl glyceryl ethers having a straight-chain alkyl group having 6 to 8 carbons, and monoalkyl glyceryl ethers having a branched alkyl group having 6 to 8 carbons, the mass ratio between the component (A) and the component (B) is then more preferably 1:20 to 1:200 and still more preferably 1:50 to 1:180. In addition, when, for example, the component (A) is a monoalkyl glyceryl ether having a cycloalkyl group having 6 to 8 carbons, the mass ratio between the component (A) and the component (B) is more preferably 1:15 to 1:150 and still more preferably 1:15 to 1:100. When the mass ratio between the contents of the component (A) and the component (B) is in the indicated range, the antimicrobial effect of the component (A) can be particularly enhanced by the component (B) and a particularly good antimicrobial activity is then obtained for the antimicrobial composition—even without a high concentration of the component (A)—due to this synergetic effect. When either component is composed of two or more compounds, the mass ratio is calculated using the total mass thereof as the content of the particular component.

There are no particular limitations on the pH of the antimicrobial composition according to the present invention, but, from the standpoint of safety and storage stability, it is preferably 2 to 12 and is more preferably 3 to 11.

The antimicrobial composition according to the present invention can be used for the same intended applications as known antimicrobial agents, antifungal agents, antiseptics and disinfectants; for example, it can be used in cosmetics, cleansers for medical care, household cleansers, and cleansers in the food industry, as an antimicrobial agent for the antimicrobial treatment of synthetic resins and daily necessities as well as household sundries, in water-based and non-water-based paints, in softeners for medical care, and so forth. However, due to its high level of safety for the human body, the antimicrobial composition according to the present invention can be advantageously used in applications, such as cosmetics, where direct contact with the human body occurs.

There are no particular limitations on the method for using the antimicrobial composition according to the present invention, and, for example, the following methods may be used: spraying or coating the target object on which an antimicrobial treatment is to be executed; application to the target object with the antimicrobial composition impregnated in, e.g., a base fabric; impregnation into the target object; immersion of the target object; incorporation or blending during molding or preparation of the target object; and so forth. In addition, the antimicrobial composition according to the present invention may contain, within a range in which the effects of the present invention are not impaired, other components in conformity to the particular embodiment.

The cosmetic according to the present invention is a cosmetic that contains the antimicrobial composition according to the present invention. This cosmetic can be exemplified by face cleansing creams, face cleansing foams, cleansing creams, cleansing milks, cleansing lotions, massage creams, cold creams, moisturizing creams, shaving creams, sunscreen creams, hair nourishing agents, hair creams, hair liquids, setting lotions, hair bleaches, color rinses, permanent wave solutions, hand creams, lipsticks, various packs, foundations, lotions, skin care lotions, emulsions, eau de colognes, nail cosmetics, chemical solutions for hygiene products such as wet wipes and antibacterial sheets, and so forth.

The content of the antimicrobial composition in the cosmetic according to the present invention should be an amount that enables the expression of the desired antimicrobial activity, but is not otherwise particularly limited and can be adjusted as appropriate in conformity with the application. However, viewed from the standpoint of coexistence between the antimicrobial activity and safety, the content of component (A), with reference to the total mass of the cosmetic, is preferably 0.001 to 10 mass %, more preferably 0.01 to 3 mass %, and most preferably 0.1 to 2 mass %. At this time, and viewed from the standpoint of an effective coexistence between the safety and the antimicrobial activity of the cosmetic through a specific enhancement of the antimicrobial activity of component (A), the content of component (B), with reference to the total mass of the cosmetic, is preferably 1 to 50 mass %, more preferably 4 to 30 mass %, still more preferably 5 to 20 mass %, even more preferably 5 to 15 mass %, and particularly preferably 5 to 10 mass %.

The cosmetic according to the present invention may contain, in conformity with the intended use and within a range in which the effects of the antimicrobial composition of the present invention are not impaired, other components in order to improve various properties (e.g., solubility, dispersibility, stability, use sensation, coatability, permeability, moisturizing action, safety, designability, optical properties, fragrance, whitening ability, and so forth) during storage, during use, or after use. For example, one or more of the following may be incorporated as appropriate on an optional basis: powder components, liquid oils and fats, solid oils and fats, waxes, hydrocarbons, higher fatty acids, higher alcohols, esters, silicones, anionic surfactants, cationic surfactants, amphoteric surfactants, nonionic surfactants, moisturizing agents, water-soluble polymers, chelating agents, lower alcohols, polyhydric alcohols (excluding the component (A) and component (B) in the present invention), monosaccharides, oligosaccharides, polysaccharides, amino acids, organic amines, polymer emulsions, pH modifiers, skin nutrients, vitamins, antioxidants, and so forth. In the following, "POE" refers to "polyoxyethylene" and "POP" refers to "polyoxypropylene".

The powder components can be exemplified by inorganic powders (for example, talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, metal salts of tungstic acid, magnesium, silica, zeolite, barium sulfate, calcium sulfate hemihydrate (exsiccated calcium sulfate), calcium phosphate, fluorapatite, hydroxyapatite, ceramic powder, metal soaps (for example, zinc myristate, calcium palmitate, and aluminum stearate), and boron nitride); organic powders (for example, polyamide resin powder (nylon powder), polyethylene powder, polymethyl methacrylate powder, polystyrene powder, styrene/acrylic acid copolymer resin powder, benzoguanamine resin powder, polytetrafluoroethylene powder, and cellulose powder); inorganic white pigments (for example, titanium dioxide and zinc oxide); inorganic red pigments (for example, iron oxide (bengara) and iron titanate); inorganic brown pigments (for example, γ-iron oxide); inorganic yellow pigments (for example, yellow iron oxide and ochre); inorganic black pigments (for example, black iron oxide and substoichiometric titanium oxide); inorganic purple pigments (for example, manganese violet and cobalt violet); inorganic green pigments (for example, chromium oxide, chromium hydroxide, and cobalt titanate); inorganic blue pigments (for example, ultramarine and Prussian blue); pearlescent pigments (for example, titanium oxide-coated mica, titanium oxide-coated bismuth oxychloride, titanium oxide-coated talc, colored titanium oxide-coated mica, bismuth oxychloride, and fish scale foil); metal powder pigments (for example, aluminum powder and copper powder); organic pigments, e.g., zirconium, barium, and aluminum lakes (for example, organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, and Blue No. 404, and also Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1); and natural colorants (chlorophyll and β-carotene).

The liquid oils and fats can be exemplified by avocado oil, camellia oil, turtle oil, macadamia nut oil, corn oil, mink oil, olive oil, rapeseed oil, egg yolk oil, sesame oil, persic oil, wheat germ oil, sasanqua oil, castor oil, flaxseed oil, safflower oil, cottonseed oil, perilla oil, soybean oil, peanut oil, tea seed oil, Japanese nutmeg oil, rice bran oil, China wood oil, Japanese tung oil, jojoba oil, germ oil, and triglycerin.

The solid oils and fats can be exemplified by cocoa butter, coconut oil, hydrogenated coconut oil, palm oil, palm kernel oil, *Rhus succedanea* kernel oil, hydrogenated oils, *Rhus succedanea* fruit wax, and hydrogenated castor oil.

The waxes can be exemplified by beeswax, candelilla wax, cotton wax, carnauba wax, bayberry wax, insect wax, spermaceti, montan wax, rice bran wax, lanolin, kapok wax, lanolin acetate, liquid lanolin, sugarcane wax, isopropyl lanolin fatty acid ester, hexyl laurate, reduced lanolin, jojoba wax, hardened lanolin, shellac wax, POE lanolin alcohol ether, POE lanolin alcohol acetate, POE cholesterol ether, polyethylene glycol lanolin fatty acid ester, and POE hydrogenated lanolin alcohol ether.

The hydrocarbon oils can be exemplified by liquid paraffin, ozocerite, squalane, pristane, paraffin, ceresin, squalene, petrolatum, and microcrystalline wax.

The higher fatty acids can be exemplified by lauric acid, myristic acid, palmitic acid, stearic acid, behenic acid, oleic acid, undecylenic acid, tall oil fatty acids, isostearic acid, linoleic acid, linolenic acid, eicosapentaenoic acid (EPA), and docosahexaenoic acid (DHA).

The higher alcohols can be exemplified by straight-chain alcohols (for example, lauryl alcohol, cetyl alcohol, stearyl alcohol, behenyl alcohol, myristyl alcohol, oleyl alcohol, and cetostearyl alcohol) and branched-chain alcohols (for example, 2-decyltetradecanol, lanolin alcohol, cholesterol, phytosterol, hexyldodecanol, isostearyl alcohol, and octyldodecanol).

The ester oils can be exemplified by isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, di-2-ethylhexanoylglycerol, dipentaerythritol/fatty acid esters, monoisostearoylglycerol, neopentyl glycol dicaprate, diisostearyl malate, di-2-heptylundecanoylglycerol, trimethylolpropane tri-2-ethylhexanoate, trimethylolpropane triisostearate, pentaerythritol tetra-2-ethylhexanoate, tri-2-ethylhexanoylglycerol, trioctanoylglycerol, triisopalmitoylglycerol, trimethylolpropane triisostearate, cetyl 2-ethylhexanoate, 2-ethylhexyl palmitate, trimyristoylglycerol, tri-2-heptylundecanoylglycerol, methyl esters of castor oil fatty acids, oleyl oleate, acetoglyceride, 2-heptylundecyl palmitate, diisobutyl adipate, 2-octyldecyl ester of N-lauroyl-L-glutamic acid, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, and 2-ethylhexyl succinate.

The silicone oils can be exemplified by chain polysiloxanes (for example, dimethylpolysiloxane, methylphenylpolysiloxane, and diphenylpolysiloxane), cyclic polysiloxanes (for example, octamethylcyclotetrasiloxane, decamethylcyclopentasiloxane, and dodecamethylcyclohexasiloxane); silicone resins that form a three-dimensional network structure, silicone rubbers, and various modified polysiloxanes (amino-modified polysiloxane, polyether-modified polysiloxane, alkyl-modified polysiloxane, and fluorine-modified polysiloxane).

The anionic surfactants can be exemplified by fatty acid soaps (for example, sodium laurate and sodium palmitate); higher alkyl sulfate ester salts (for example, sodium lauryl sulfate and potassium lauryl sulfate); alkyl ether sulfate ester salts (for example, POE-lauryl sulfate/triethanolamine salt and sodium POE-lauryl sulfate); N-acylsarcosinic acid (for example, sodium lauroylsarcosinate); higher fatty acid amide sulfonate salts (for example, sodium N-myristoyl-N-methyltaurate, sodium cocofatty acid methyltaurate, and sodium laurylmethyltaurate); phosphate ester salts (sodium POE-oleyl ether phosphate, POE-stearyl ether phosphate, and so on); sulfosuccinate salts (for example, sodium di-2-ethylhexyl sulfosuccinate, sodium monolauroyl monoethanolamide polyoxyethylene sulfosuccinate, and sodium lauryl polypropylene glycol sulfosuccinate); alkylbenzenesulfonate salts (for example, sodium linear dodecylbenzenesulfonate, triethanolamine salt of linear dodecylbenzenesulfonic acid, and linear dodecylbenzenesulfonic acid); salts of higher fatty acid ester sulfate esters (for example, sodium hardened cocofatty acid glycerol ester sulfate); N-acylglutamate salts (for example, monosodium N-lauroylglutamate, disodium N-stearoylglutamate, and monosodium N-myristoyl-L-glutamate); sulfated oils (for example, Turkey red oil); POE-alkyl ether carboxylic acids; POE-alkylallyl ether carboxylate salts; α-olefinsulfonate salts; higher fatty acid ester sulfonate salts; secondary-alcohol sulfate ester salts; higher fatty acid alkylolamide sulfate ester salts; sodium lauroylmonoethanolamide succinate; ditriethanolamine salt of N-palmitoylaspartic acid; and sodium caseinate.

The cationic surfactants can be exemplified by alkyltrimethylammonium salts (for example, stearyltrimethylammonium chloride and lauryltrimethylammonium chloride), alkylpyridinium salts (for example, cetylpyridinium chloride), dialkyldimethylammonium salts such as distearyldimethylammonium chloride, poly(N,N'-dimethyl-3,5-methylenepiperidinium chloride), alkyl quaternary ammonium salts, alkyldimethylbenzylammonium salts, alkylisoquinolinium salts, dialkylmorpholinium salts, POE-alkylamines, alkylamine salts, polyamine/fatty acid derivatives, amyl alcohol/fatty acid derivatives, benzalkonium chloride, and benzethonium chloride.

The amphoteric surfactants can be exemplified by imidazoline-based amphoteric surfactants (for example, sodium 2-undecyl-N,N,N-(hydroxyethylcarboxymethyl)-2-imidazoline and 2-cocoyl-2-imidazolinium hydroxide-1-carboxyethyloxy disodium salt); and betaine-based surfactants (for example, 2-alkyl-N-carboxymethyl-N-hydroxyethylimidazolinium betaine (Na cocoamphoacetate), lauryldimethylaminoacetate betaine, alkylbetaines, amidobetaines, and sulfobetaines).

The nonionic surfactants can be exemplified by sorbitan fatty acid esters (for example, sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate); glycerol/polyglycerol fatty acids (for example, glycerol monocottonseed oil fatty acids, glycerol monoerucate, glycerol sesquioleate, glycerol monostearate, glycerol α,α'-oleate pyroglutamate, and glycerol monostearate malate); propylene glycol/fatty acid esters (for example, propylene glycol monostearate); hardened castor oil derivatives; glycerol alkyl ethers; POE-sorbitan/fatty acid esters (for example, POE-sorbitan monooleate, POE-sorbitan monostearate, and POE-sorbitan tetraoleate); POE-sorbitol/fatty acid esters (for example, POE-sorbitol monolaurate, POE-sorbitol monooleate, POE-sorbitol pentaoleate, and POE-sorbitol monostearate); POE-glycerol/fatty acid esters (for example, POE-glycerol monostearate, POE-glycerol monoisostearate, POE-glycerol triisostearate, POE-monooleate); POE-fatty acid esters (for example, POE-distearate, POE-dioleate, and ethylene glycol distearate); POE-alkyl ethers (for example, POE-lauryl ether, POE-oleyl ether, POE-stearyl ether, POE-behenyl ether, POE-2-octyl-dodecyl ether, and POE-cholestanol ether); Pluronic types (for example, Pluronic); POE/POP-alkyl ethers (for example, POE/POP-cetyl ether, POE/POP-2-decyltetradecyl ether, POE/POP-monobutyl ether, POE/POP-hydrogenated lanolin, and POE/POP-glycerin ether); tetra-POE/tetra-POP-ethylenediamine condensates (for example, Tetronic); POE-castor oil/hardened castor oil derivatives (for example, POE-castor oil, POE-hardened castor oil, POE-hardened castor oil monoisostearate, POE-hardened castor oil triisostearate, POE-hardened castor oil monopyroglutamate monoisostearate diester, and POE-hardened castor oil maleate); POE-beeswax.lanolin derivatives (for example, POE-sorbitol beeswax); alkanolamides (for example, cocofatty acid diethanolamides, lauric monoethanolamide, and fatty acid isopropanolamides); POE-propylene glycol fatty acid esters; POE-alkylamines; POE-fatty acid amides; sucrose fatty acid esters; alkylethoxydimethylamine oxides; and trioleyl phosphate.

The moisturizing agents can be exemplified by polyethylene glycol, xylitol, sorbitol, maltitol, chondroitin sulfate, hyaluronic acid, mucoitin sulfate, charonic acid, atelocollagen, cholesteryl 12-hydroxystearate, sodium lactate, bile acid salts, dl-pyrrolidonecarboxylate salts, short-chain soluble collagen, (EO)PO adducts of diglycerol, Izayoi rose extract, yarrow extract, and merirot extract.

Natural water-soluble polymers can be exemplified by plant-derived polymers (for example, gum arabic, tragacanth gum, galactan, guar gum, carob gum, karaya gum, carrageenan, pectin, agar, quince seed (marmelo), algae colloids (brown algae extract), starch (rice, corn, potato, and wheat), and glycyrrhizic acid); microorganism-derived polymers (for example, xanthan gum, dextran, succinoglucan, pullulan, and gellan gum); and animal-derived polymers (for example, collagen, casein, albumin, and gelatin).

Water-soluble polymers can be exemplified by starch polymers (for example, carboxymethyl starch and methyl hydroxypropyl starch); cellulosic polymers (for example, methyl cellulose, ethyl cellulose, methyl hydroxypropyl cellulose, hydroxyethyl cellulose, sodium cellulose sulfate, hydroxypropyl cellulose, carboxymethyl cellulose, sodium carboxymethyl cellulose, crystalline cellulose, and cellulose powder); alginic acid polymers (for example, sodium alginate and the propylene glycol ester of alginic acid); vinyl polymers (for example, polyvinyl alcohol, polyvinyl methyl ether, polyvinylpyrrolidone, and carboxyvinyl polymers); polyoxyethylene polymers (for example, polyoxyethylene-polyoxypropylene copolymers prepared from polyethylene glycol 20,000, 40,000 or 60,000); acrylic polymers (for example, sodium polyacrylate, polyethyl acrylate, and polyacrylamide); polyethyleneimine, and cationic polymers.

The chelating agents can be exemplified by 1-hydroxyethane-1,1-diphosphonic acid, tetrasodium 1-hydroxyethane-1,1-diphosphonate, disodium edetate, trisodium edetate, tetrasodium edetate, sodium polyphosphate, sodium meta-phosphate, phosphoric acid, ascorbic acid, succinic acid, and edetic acid.

The lower alcohols can be exemplified by ethanol, propanol, isopropanol, isobutyl alcohol, and t-butyl alcohol.

The polyhydric alcohols (but excluding the component (A) and component (B) according to the present invention) can be exemplified by dihydric alcohols (for example, 1,2-ethanediol, 1,2-propanediol, 1,3-propanediol, 1,2-butanediol, 1,3-butanediol, 1,4-butanediol, 2,3-butanediol, 1,2-pentanediol, 1,5-pentanediol, and 2,4-pentanediol); trihydric alcohols (for example, glycerol and trimethylolpropane); tetrahydric alcohols (for example, 1,2,5,6-hexanetetrol and pentaerythritol); pentahydric alcohols (for example, xylitol); hexahydric alcohols (for example, sorbitol and mannitol); polyhydric alcohol polymers (for example, diethylene glycol, triethylene glycol, dipropylene glycol, polypropylene glycol, tetraethylene glycol, diglycerol, polyethylene glycol, triglycerol, tetraglycerol, and polyglycerol); alcohol alkyl ethers (for example, ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether, diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether); dihydric alcohol ether esters (for example, ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate); sugar alcohols (for example, sorbitol, maltitol, maltotriose, mannitol, sucrose, erythritol, glucose, fructose, sugars provided by the hydrolysis of starch, maltose, xylitose, and alcohols prepared by reducing sugars provided by the hydrolysis of starch); glysolid; tetrahydrofurfuryl alcohol; POE-tetrahydrofurfuryl alcohol; POP-butyl ether, POP-.POE-butyl ether; tripolyoxypropylene glycerol ether; POP-glycerol ether; POP-glycerol ether phosphate; POP/POE-pentaerythritol ether, and polyglycerol.

The monosaccharides can be exemplified by trioses (for example, D-glyceryl aldehyde and dihydroxy acetone); tetroses (for example, D-erythrose, D-erythrulose, D-threose, and erythritol); pentoses (for example, L-arabinose, D-xylose, L-lyxose, D-arabinose, D-ribose, D-ribulose, D-xylulose, and L-xylulose); hexoses (for example, D-glucose, D-talose, D-psicose, D-galactose, D-fructose, L-galactose, L-mannose, and D-tagatose); heptoses (for example, aldoheptose and hepulose); octoses (for example, octulose); deoxysaccharides (for example, 2-deoxy-D-ribose, 6-deoxy-L-galactose, and 6-deoxy-L-mannose); aminosaccharides (for example, D-glucosamine, D-galactosamine, sialic acid, aminouronic acid, and muramic acid); uronic acids (for example, D-glucuronic acid, D-mannuronic acid, L-guluronic acid, D-galacturonic acid, and L-iduronic acid).

The oligosaccharides can be exemplified by sucrose, umbelliferose, lactose, planteose, isolichnoses, α,α-trehalose, raffinose, lichnoses, umbilicin, stachyose, verbascoses.

The polysaccharides can be exemplified by cellulose, quince seed, chondroitin sulfate, starch, galactan, dermatan sulfate, glycogen, gum arabic, heparan sulfate, hyaluronic acid, tragacanth gum, keratan sulfate, chondroitin, xanthan gum, mucoitin sulfate, guar gum, dextran, keratosulfate, locust bean gum, succinoglucan, and charonic acid.

The amino acids can be exemplified by neutral amino acids (for example, threonine and cysteine); and basic amino acids (for example, hydroxylysine). Amino acid derivatives can be exemplified by sodium acylsarcosinate (sodium lauroylsarcosinate), acylglutamate salts, sodium acyl-β-alanine, glutathione, and pyrrolidonecarboxylic acid.

The organic amines can be exemplified by monoethanolamine, diethanolamine, triethanolamine, morpholine, triisopropanolamine, 2-amino-2-methyl-1,3-propanediol, and 2-amino-2-methyl-1-propanol.

The polymer emulsions can be exemplified by acrylic resin emulsions, polyethyl acrylate emulsions, acrylic resin liquids, polyalkyl acrylate emulsions, polyvinyl acetate resin emulsions, and natural rubber latexes.

The pH modifiers can be exemplified by lactic acid-sodium lactate, succinic acid-sodium succinate, citric acid-sodium citrate, and sodium bicarbonate. The pH of the cosmetic according to the present invention should be adjusted as appropriate in conformity to the application and may be, for example, 3 to 11, with 3.0 to 7.5 being preferred from the standpoint of, e.g., applicability to the skin.

The vitamins can be exemplified by vitamins A, B1, B2, B6, C, and E and their derivatives, pantothenic acid and derivatives thereof, and biotin.

The antioxidants can be exemplified by tocopherols, dibutylhydroxytoluene, butylhydroxyanisole, and gallic acid esters.

Other blendable components can be exemplified by inflammation-reducing agents (for example, glycyrrhizinic acid derivatives, glycyrrhetinic acid derivatives, salicylic acid derivatives, hinokitiol, zinc oxide, and allantoin); skin-lightening agents (for example, *Saxifraga stolonifera* extract and arbutin); various extracts (for example, phellodendron bark, Coptis rhizome, *Lithospermum erythrorhizon* root, *Paeonia lactiflora*, Swertia herb, birch, sage, Japanese loquat, carrot, aloe, common mallow, iris, grape, coix seed, *Luffa cylindrica*, lily, saffron, Cnidium rhizome, ginger, *Hypericum erectum*, ononis, garlic, red pepper, *Citrus unshiu* peel, Japanese Angelica root, and seaweed); stimulants and activators (for example, royal jelly, photosensitizers, and cholesterol derivatives); blood circulation promoters (for example, benzyl nicotinate, β-butoxyethyl nicotinate, capsaicin, zingerone, cantharide tincture, ichthammol, tannic acid, α-borneol, tocopherol nicotinate, inositol hexanicotinate, cyclandelate, cinnarizine, tolazoline, acetylcholine, verapamil, cepharanthine, and γ-oryzanol); antiseborrheic agents (for example, sulfur and thianthol); and anti-inflammatory agents (for example, tranexamic acid, thiotaurine, and hypotaurine).

EXAMPLES

The present invention is specifically described in the following examples. Unless specifically indicated otherwise, "%" in the following examples, etc. is on a mass basis.

Examples 1 to 27 and Comparative Examples 1 to 9

<Compounds Used>
Component (A)
  A-1: 2-ethylhexyl glyceryl ether
  A-2: octyl glyceryl ether
  A-3: cyclohexyl glyceryl ether
Component (B)
  B-1: 2-methyl-1,3-propanediol
  B-2: tripropylene glycol
  B-3: 3-methyl-1,3-butanediol
Component (C) (Comparative Component)
  C-1: propylene glycol
  C-2: dipropylene glycol
  C-3: 1,3-butanediol
<Test Microorganisms>
  E. coli: *Escherichia coli* (bacteria) ATCC 8739
  P. aer: *Pseudomonas aeruginosa* (bacteria) ATCC 9027
  S. aur: *Staphylococcus aureus* (bacteria) ATCC 6538
  C. alb: *Candida albicans* (yeast) ATCC 10231
  A. bra: *Aspergillus brasiliensis* (fungus) ATCC 16404
  <Preparation of Test Solutions>
  Test solutions containing these microorganisms were prepared as follows: the bacteria were precultured on SCD (soybean casein digest) liquid medium and the yeast and fungus were precultured on glucose agar medium; this was followed in each case by adjustment of the microorganism concentration in the liquids to the level of $10^6$ to $10^7$ cfu/mL using 0.9% aqueous NaCl solution.
  <Test Method>
  20 μL of each test solution was dispensed onto a microplate; 180 μL of each antimicrobial composition—prepared by the dilution with medium of component (B) and component (C) at the prescribed concentrations given in Table 1 and component (A) at various concentrations was added; and stirring was carried out to provide a mixed solution (the test sample). Component (A), component (B), and component (C) were prepared here so as to provide the prescribed concentrations in mass % in the mixed solutions. Each mixed solution was then cultured as follows: 48 hours in a thermostat at 33° C. for the bacterial mixed solutions; 3 days at 25° C. for the yeast mixed solutions; and 1 week at 25° C. for the fungus mixed solutions. The post-culture turbidity of each mixed solution was observed. For each microorganism, the mixed solutions containing component (A) at the various concentrations, and each blending condition for component (B) or component (C) (each of the mixed solutions), those mixed solutions were identified where turbidity or the presence of colonies/filaments was not seen (i.e., mixed solutions where growth of the test microorganism had been stopped). For each of the five microorganisms, the lowest component (A) concentration in the mixed solutions where growth had been stopped was designated the minimum inhibitory concentration. The concentration at which growth was stopped for all five of the test microorganisms (i.e., the highest concentration among the minimum inhibitory concentrations for the five microorganisms) was designated the five-species minimum inhibitory concentration (five-species MIC). The mass ratio (A):(B) between component (A) and component (B) was calculated in each example for the five-species MIC preparation conditions. The preparation conditions and test results for each antimicrobial composition are given in Table 1 to Table 3. Numerical values having a "+" appended to the numerical value for the MIC indicate that the numerical value of the MIC was at least said concentration (within the test range, growth of the microorganism was not stopped even under the condition at the highest prepared concentration), while numerical values having a "−" appended to the numerical value for the MIC indicate that the MIC concentration was less than said concentration (within the test range, growth of the microorganism was stopped even under the condition of the lowest prepared concentration). In addition, the antimicrobial activity (enhancement effect) was evaluated also using the numerical MIC values given in those instances where a "+" or "−" is provided.

TABLE 1

|  |  | Comp. Ex. 1 | Example 1 | Example 2 | Example 3 | Example 4 | Example 5 | Example 6 |
|---|---|---|---|---|---|---|---|---|
| component (B) (%) | B-1 |  | 5 | 10 | 15 |  |  |  |
|  | B-2 |  |  |  |  | 5 | 10 | 15 |
|  | B-3 |  |  |  |  |  |  |  |
| component (C) (%) | C-1 |  |  |  |  |  |  |  |
|  | C-2 |  |  |  |  |  |  |  |
|  | C-3 |  |  |  |  |  |  |  |
| component (A) medium | | A-1 balance | A-1 balance | A-1 balance | A-1 balance | A-1 balance | A-1 balance | A-1 balance |
| five-species MIC (%) | | 1.00+ | 0.38 | 0.09− | 0.09− | 0.38 | 0.19 | 0.09− |
| (A):(B) (five-species MIC preparation) | | — | 1:13.1 | 1:111 | 1:167 | 1:13.1 | 1:52.6 | 1:167 |
| antimicrobial activity | | — | ◯ | ◯◯ | ◯◯ | ◯ | ◯ | ◯◯ |

|  |  | Example 7 | Example 8 | Example 9 | Comp. Ex. 2 | Comp. Ex. 3 | Comp. Ex. 4 |
|---|---|---|---|---|---|---|---|
| component (B) (%) | B-1 |  |  |  |  |  |  |
|  | B-2 |  |  |  |  |  |  |
|  | B-3 | 5 | 10 | 15 |  |  |  |
| component (C) (%) | C-1 |  |  |  | 5 |  |  |
|  | C-2 |  |  |  |  | 5 |  |
|  | C-3 |  |  |  |  |  | 5 |

TABLE 1-continued

|  | | | | | | |
|---|---|---|---|---|---|---|
| component (A) medium | A-1 balance | A-1 balance | A-1 balance | A-1 balance | A-1 balance | A-1 balance |
| five-species MIC (%) | 0.38 | 0.19 | 0.09− | 1.00+ | 1.00+ | 1.00+ |
| (A):(B) (five-species MIC preparation) | 1:13.1 | 1:52.6 | 1:167 | — | — | — |
| antimicrobial activity | ○ | ○ | ○○ | X | X | X |

Criteria for Evaluating Antimicrobial Activity (Enhancement Effect)

Evaluation using the five-species MIC value, using the five-species MIC value for only component A-1 (Comparative Example 1) as the basis.

OO: the five-species MIC is less than 0.1-times Comp. Ex. 1

O: the five-species MIC is at least 0.1-times, but less than 0.5-times Comp. Ex. 1

Δ: the five-species MIC is at least 0.5-times, but less than 1.0-times Comp. Ex. 1

X: the five-species MIC is at least 1.0-times Comp. Ex. 1

Criteria for Evaluating Antimicrobial Activity (Enhancement Effect)

Evaluation using the five-species MIC value and using the five-species MIC value for only component A-2 (Comparative Example 5) as reference.

OO: the five-species MIC is less than 0.1-times Comp. Ex.

O: the five-species MIC is at least 0.1-times, but less than 0.5-times Comp. Ex. 5

Δ: the five-species MIC is at least 0.5-times, but less than 1.0-times Comp. Ex. 5

X: the five-species MIC is at least 1.0-times Comp. Ex. 5

TABLE 2

|  |  | Comp. Ex. 5 | Example 10 | Example 11 | Example 12 | Exammie 13 | Example 14 | Example 15 |
|---|---|---|---|---|---|---|---|---|
| component (B) (%) | B-1 |  | 5 | 10 | 15 |  |  |  |
|  | B-2 |  |  |  |  | 5 | 10 | 15 |
|  | B-3 |  |  |  |  |  |  |  |
| component (C) (%) | C-1 |  |  |  |  |  |  |  |
|  | C-2 |  |  |  |  |  |  |  |
|  | C-3 |  |  |  |  |  |  |  |
| component (A) medium | | A-2 balance | A-2 balance | A-2 balance | A-2 balance | A-2 balance | A-2 balance | A-2 balance |
| five-species MIC (%) | | 0.50+ | 0.09 | 0.05− | 0.05− | 0.09 | 0.05− | 0.05− |
| (A):(B) (five-species MIC preparation) | | — | 1:55.6 | 1:200 | 1:300 | 1:55.6 | 1:200 | 1:300 |
| antimicrobial activity | | — | ○ | ○○ | ○○ | ○ | ○○ | ○○ |

|  |  | Example 16 | Exammle 17 | Example 18 | Comp. Ex. 6 | Comp. Ex. 7 | Comp. Ex. 8 |
|---|---|---|---|---|---|---|---|
| component (B) (%) | B-1 |  |  |  |  |  |  |
|  | B-2 |  |  |  |  |  |  |
|  | B-3 | 5 | 10 | 15 |  |  |  |
| component (C) (%) | C-1 |  |  |  | 5 |  |  |
|  | C-2 |  |  |  |  | 5 |  |
|  | C-3 |  |  |  |  |  | 5 |
| component (A) medium | | A-2 balance | A-2 balance | A-2 balance | A-2 balance | A-2 balance | A-2 balance |
| five-species MIC (%) | | 0.13 | 0.05− | 0.05− | 0.50+ | 0.50+ | 0.50+ |
| (A):(B) (five-species MIC preparation) | | 1:38.5 | 1:200 | 1:300 | — | — | — |
| antimicrobial activity | | ○ | ○○ | ○○ | X | X | X |

TABLE 3

| | | Comp. Ex. 9 | Example 19 | Example 20 | Example 21 | Example 22 | Example 23 |
|---|---|---|---|---|---|---|---|
| component (B) (%) | B-1 | | 5 | 10 | 15 | | |
| | B-2 | | | | | 5 | 10 |
| | B-3 | | | | | | |
| component (C) (%) | C-1 | | | | | | |
| | C-2 | | | | | | |
| | C-3 | | | | | | |
| component (A) medium | | A-3 balance | A-3 balance | A-3 balance | A-3 balance | A-3 balance | A-3 balance |
| five-species MIC (%) | | 3.00 | 1.50 | 0.19– | 0.19– | 2.00 | 1.50 |
| (A):(B) (five-species MIC preparation) | | — | 1:3.33 | 1:52.6 | 1:78.9 | 1:2.50 | 1:6.67 |
| antimicrobial activity | | — | Δ | ○○ | ○○ | Δ | Δ |

| | | Example 24 | Example 25 | Example 26 | Example 27 |
|---|---|---|---|---|---|
| component (B) (%) | B-1 | | | | |
| | B-2 | 15 | | | |
| | B-3 | | 5 | 10 | 15 |
| component (C) (%) | C-1 | | | | |
| | C-2 | | | | |
| | C-3 | | | | |
| component (A) medium | | A-3 balance | A-3 balance | A-3 balance | A-3 balance |
| five-species MIC (%) | | 1.00 | 2.00 | 2.00 | 0.19– |
| (A):(B) (five-species MIC preparation) | | 1:15.0 | 1:2.50 | 1:5.00 | 1:78.9 |
| antimicrobial activity | | ○ | Δ | Δ | ○○ |

Criteria for Evaluating Antimicrobial Activity (Enhancement Effect)

Evaluation using the five-species MIC value and using the five-species MIC value for only component A-3 (Comparative Example 9) as reference.

○○: the five-species MIC is less than 0.1-times Comp. Ex.

○: the five-species MIC is at least 0.1-times, but less than 0.5-times Comp. Ex. 9

Δ: the five-species MIC is at least 0.5-times, but less than 1.0-times Comp. Ex. 9

X: the five-species MIC is at least 1.0-times Comp. Ex. 9

In accordance with the preceding results, an antimicrobial activity-enhancing effect and an improved antimicrobial activity were observed for the antimicrobial compositions that used both component (A) and component (B), which, however, were not seen in the examples that used component (C), a comparative component, in place of component (B). It was thereby shown for the antimicrobial composition according to the present invention that the antimicrobial effect of component (A) was substantially enhanced by the addition of component (B) and a high antimicrobial activity was then expressed.

Examples 28 to 33 and Comparative Examples 10 to 17

<Compounds Used>
Component (A)
  A-4: 1,2-octanediol
  A-5: hexyl glyceryl ether Component (B)
  B-1: 2-methyl-1,3-propanediol
  B-2: tripropylene glycol
  B-3: 3-methyl-1,3-butanediol
Component (C) (Comparative Component)
  C-1: propylene glycol
  C-2: dipropylene glycol
  C-3: 1,3-butanediol
<Test Bacteria>
  E. coli: Escherichia coli (bacteria) ATCC 8739
  P. aer: Pseudomonas aeruginosa (bacteria) ATCC 9027
<Preparation of Test Solutions>

Test solutions containing these microorganisms were prepared by preculture on SCD liquid medium followed by adjusting the microorganism concentration in the liquids to the level of $10^6$ to $10^7$ cfu/mL using a 0.9% aqueous NaCl solution.

<Test Method>

20 μL of each test solution was dispensed onto a microplate; 180 μL of each antimicrobial composition—prepared by the dilution with medium of component (B) and component (C) at the prescribed concentrations and component (A) at various concentrations—was added; and stirring was carried out to provide a mixed solution (the test sample). Component (A), component (B), and component (C) were prepared here so as to provide the prescribed concentrations in mass % in the mixed solutions. Each mixed solution was then cultured for 48 hours in a thermostat at 33° C., after which the turbidity of each mixed solution was observed. For each bacteria, the mixed solutions containing component (A) at the various concentrations, and each blending condition for component (B) or component (C) (each of the mixed solutions), the lowest concentration of component (A) was identified for the mixed solutions where turbidity or the presence of colonies/filaments was not seen (i.e., mixed solutions where growth of the test bacteria had been stopped), and was designated the minimum inhibitory concentration (MIC) for the particular bacteria. The preparation conditions and test results for each antimicrobial composition are given in Table 4.

index of 1.0 or more indicates that there is a simple additive effect or an antagonistic effect on the antimicrobial activity.

$$FIC = A_1/A_0 + B_1/B_0$$

In the formula, $A_0$ represents the MIC value for the use of component (A) by itself; $A_1$ represents the concentration of component (A) at the MIC for the case of combined use with

TABLE 4

|  |  | Comp. Ex. 10 | Ex. 28 | Ex. 29 | Ex. 30 | Comp. Ex. 11 | Comp. Ex. 12 | Comp. Ex. 13 | Comp. Ex. 14 |
|---|---|---|---|---|---|---|---|---|---|
| component (B) (%) | B-1 |  | 5 |  |  |  |  |  |  |
|  | B-2 |  |  | 5 |  |  |  |  |  |
|  | B-3 |  |  |  | 5 |  |  |  |  |
| component (C) (%) | C-1 |  |  |  |  | 5 |  |  |  |
|  | C-2 |  |  |  |  |  | 5 |  |  |
|  | C-3 |  |  |  |  |  |  | 5 |  |
| medium |  | balance | balance | balance | balance | balance | balance | balance | balance |
| component (A) |  | A-4 | A-4 | A-4 | A-4 | A-4 | A-4 | A-4 | A-5 |
| MIC (%) | E. coli | 0.13 | 0.09– | 0.09– | 0.09– | 0.13 | 0.13 | 0.19 | 0.25 |
|  | P. aer | 0.38 | 0.09– | 0.09– | 0.09– | 0.38 | 0.38 | 0.38 | 0.75 |

|  |  | Ex. 31 | Ex. 32 | Ex. 33 | Comp. Ex. 15 | Comp. Ex. 16 | Comp. Ex. 17 |
|---|---|---|---|---|---|---|---|
| component (B) (%) | B-1 | 5 |  |  |  |  |  |
|  | B-2 |  | 5 |  |  |  |  |
|  | B-3 |  |  | 5 |  |  |  |
| component (C) (%) | C-1 |  |  |  | 5 |  |  |
|  | C-2 |  |  |  |  | 5 |  |
|  | C-3 |  |  |  |  |  | 5 |
| medium |  | balance | balance | balance | balance | balance | balance |
| component (A) |  | A-5 | A-5 | A-5 | A-5 | A-5 | A-5 |
| MIC (%) | E. coli | 0.19 | 0.19 | 0.19 | 0.25 | 0.25 | 0.25 |
|  | P. aer | 0.09– | 0.09– | 0.09– | 1.00 | 0.75 | 1.00 |

In accordance with the preceding results, an antimicrobial performance-enhancing effect and an improved antimicrobial activity were observed for the antimicrobial compositions that used both component (A) and component (B), which, however, were not seen in the examples that used component (C), a comparative component, in place of component (B). It was thereby shown for the antimicrobial composition according to the present invention that the antimicrobial effect of component (A) was substantially enhanced by the addition of component (B) and a high antimicrobial activity was then expressed.

Examples 34 to 37

<Evaluation 1 of Enhancing Effect on Antimicrobial/Antifungal Activity>

In order to evaluate the enhancing effect for the antimicrobial composition according to the present invention, MICs were measured by the same method as in Example 1, but changing the constitution of the antimicrobial composition as shown in Table 5 using the previously described component (A) and component (B), and the fractional inhibitory concentration (FIC) index was calculated with the MICs in accordance with the formula given below.

The FIC index is an index that evaluates the synergetic effect for the antimicrobial activity for compositions that contain two or more components, and a lower value of the FIC index indicates that a higher synergetic effect is present. Specifically, an FIC index of less than 1.0 indicates that there is a synergetic effect on the antimicrobial activity between the components constituting the composition, while an FIC component (B); $B_0$ represents the MIC value for the use of component (B) by itself; and $B_1$ represents the concentration of component (B) at the MIC for the case of combined use with component (A). Here, the value of the result measured for each component by itself by the same method as the test method in Example 1 was used for the MIC value of each individual component, and the concentration of each component at the MIC value measured for the antimicrobial composition was used for the concentration of each component during combined use. The results of calculation of the FIC indexes are given in Table 5. The bacteria used in the test is as follows.

P. aer: *Pseudomonas aeruginosa* (bacteria) ATCC 9027

TABLE 5

|  |  | Example 34 | Example 35 | Example 36 | Example 37 |
|---|---|---|---|---|---|
| antimicrobial composition | component B-1 (B) (%) | 5 | 5 | 5 | 5 |
|  | component (A) | A-1 | A-3 | A-4 | A-5 |
|  | medium | balance | balance | balance | balance |
| FIC index |  | 0.93 | 0.97 | 0.99 | 0.93 |

Examples 38 to 41

<Evaluation 2 of Enhancing Effect on Antimicrobial/Antifungal Activity>

In order to evaluate the enhancing effect for the antimicrobial composition according to the present invention, MIC measurement and FIC index calculation were performed for various microorganisms using the same method as in Example 34, but changing the constitution of the antimicrobial composition as shown in Table 6 using the previously described component (A) and component (B). For the FIC indexes calculated for the individual microorganisms, Table 6 gives the minimum FIC index values and the results of an overall FIC evaluation based on the following Overall FIC Index Evaluation Criteria 1. The microorganisms used in this test are given below.

S. aur: *Staphylococcus aureus* (bacteria) ATCC 6538
C. alb: *Candida albicans* (yeast) ATCC 10231
A. bra: *Aspergillus brasiliensis* (mold) ATCC 16404
Overall FIC Index Evaluation Criteria 1
OO: the FIC index is less than 1.0 in the tests for all three microorganisms
O: the FIC index is less than 1.0 in two of the tests for the three microorganisms
Δ: the FIC index is less than 1.0 in one of the tests for the three microorganisms
X: the FIC index is at least 1.0 in the tests for all three microorganisms

TABLE 6

| | | Example 38 | Example 39 | Example 40 | Example 41 |
|---|---|---|---|---|---|
| antimicrobial composition | component B-1 (B) (%) | 5 | 7 | 9 | 10 |
| | component (A) medium | A-1 balance | A-1 balance | A-1 balance | A-1 balance |
| minimum FIC index | | 0.82 | 0.97 | 0.83 | 0.76 |
| overall FIC evaluation | | O | OO | OO | OO |

Examples 42 to 49

<Evaluation 3 of Enhancing Effect on Antimicrobial/Antifungal Activity>

In order to evaluate the enhancing effect for the antimicrobial composition according to the present invention, MIC measurements and FIC index calculations were performed for various microorganisms using the same method as in Example 34, but changing the constitution of the antimicrobial composition as shown in Table 7 using the previously described component (A) and component (B). For the FIC indexes calculated for the individual microorganisms, Table 7 gives the minimum FIC index values and the results of an overall FIC evaluation based on the following Overall FIC Index Evaluation Criteria 2. The microorganisms used in this test are given below.

S. aur: *Staphylococcus aureus* (bacteria) ATCC 6538
A. bra: *Aspergillus brasiliensis* (mold) ATCC 16404
Overall FIC Index Evaluation Criteria 2
OO: the FIC index is less than 1.0 in the tests for both of the two microorganisms
O: the FIC index is less than 1.0 in one of the tests for the two microorganisms
X: the FIC index is at least 1.0 in the tests for both of the two microorganisms

TABLE 7

| | | Ex. 42 | Ex. 43 | Ex. 44 | Ex. 45 | Ex. 46 | Ex. 47 | Ex. 48 | Ex. 49 |
|---|---|---|---|---|---|---|---|---|---|
| antimicrobial composition | component B-1 (B) (%) | 5 | 7 | 9 | 10 | 5 | 7 | 9 | 10 |
| | component (A) medium | A-3 bal. | A-3 bal. | A-3 bal. | A-3 bal. | A-5 bal. | A-5 bal. | A-5 bal. | A-5 bal. |
| minimum FIC index | | 0.81 | 0.83 | 0.78 | 0.69 | 0.98 | 0.94 | 0.80 | 0.75 |
| overall FIC evaluation | | O | OO | OO | OO | O | OO | OO | OO |

The results provided above demonstrate that, due to a specific synergetic effect due to the addition of component (B), the antimicrobial effect of component (A) in the antimicrobial composition according to the present invention is substantially enhanced and a high antimicrobial activity is then exhibited. It is thought that, due to this specific synergetic effect, the antimicrobial composition of component (A) used in combination with component (B) was able to exhibit a substantial increase in the antimicrobial performance-enhancing effect and antimicrobial activity that was not seen in the examples that used component (C), a comparative component, in place of component (B).

The invention claimed is:
1. An antimicrobial composition, containing:
    a component (A) that is at least one selected from the group consisting of 1,2-alkanediols having an alkyl group having 6 to 8 carbons and monoalkyl glyceryl ethers having an alkyl group having 6 to 8 carbons; and
    a component (B) that is at least one selected from the group consisting of tripropylene glycol, 2-methyl-1,3-propanediol, and 3-methyl-1,3-butanediol,
    wherein a mass ratio between the component (A) and the component (B) in the antimicrobial composition is 1:13 to 1:300.
2. The antimicrobial composition according to claim 1, wherein the component (B) contains tripropylene glycol.
3. The antimicrobial composition according to claim 1, wherein the component (B) contains 2-methyl-1,3-propanediol.
4. The antimicrobial composition according to claim 1, wherein the component (A) is at least one selected from monoalkyl glyceryl ethers having a straight-chain alkyl group having 6 to 8 carbons.
5. A cosmetic comprising the antimicrobial composition according to claim 1.
6. The cosmetic according to claim 5, wherein a content of the component (B) in the cosmetic is 1 to 50 mass % with reference to the total mass of the cosmetic.
7. A method of enhancing an antimicrobial effect of a component (A) in a cosmetic by a component (B), the method comprising:
    adding to the cosmetic
    the component (A) wherein the component (A) is at least one selected from the group consisting of 1,2-alkanediols having an alkyl group having 6 to 8 carbons and monoalkyl glyceryl ethers having an alkyl group having 6 to 8 carbons, and the component (B) wherein the component (B) is at least one selected from the group consisting of tripropylene glycol, 2-methyl-1,3-propanediol, and 3-methyl-1,3-butanediol, wherein a mass ratio between the component (A) and the component (B) is 1:13 to 1:300.

* * * * *